US012685589B2

(12) United States Patent
Govari et al.

(10) Patent No.: US 12,685,589 B2
(45) Date of Patent: Jul. 21, 2026

(54) SYSTEM AND METHOD OF UNIPOLAR PFA

(71) Applicant: Biosense Webster (Israel) Ltd.,
Yokneam (IL)

(72) Inventors: Assaf Govari, Haifa (IL); Amit Fuchs,
Hogla (IL); Andres Claudio Altmann,
Haifa (IL)

(73) Assignee: Biosense Webster (Israel) Ltd.,
Yokneam (IL)

( * ) Notice: Subject to any disclaimer, the term of this
patent is extended or adjusted under 35
U.S.C. 154(b) by 255 days.

(21) Appl. No.: 18/539,395

(22) Filed: Dec. 14, 2023

(65) Prior Publication Data

US 2025/0195138 A1    Jun. 19, 2025

(51) Int. Cl.
*A61B 18/14*    (2006.01)
*A61B 18/16*    (2006.01)
*A61B 18/00*    (2006.01)

(52) U.S. Cl.
CPC .......... *A61B 18/16* (2013.01); *A61B 18/1492*
(2013.01); *A61B 2018/00351* (2013.01); *A61B*
*2018/00577* (2013.01); *A61B 2018/00613*
(2013.01); *A61B 2018/00642* (2013.01); *A61B*
*2018/00702* (2013.01);
(Continued)

(58) Field of Classification Search
CPC . A61B 18/1233; A61B 18/1492; A61B 18/16;
A61B 2017/00075; A61B 2018/00351;
A61B 2018/00357; A61B 2018/00577;
A61B 2018/00613; A61B 2018/00642;

A61B 2018/00702; A61B 2018/00773;
A61B 2018/124; A61B 2018/1253; A61B
2018/1465; A61B 2018/1467; A61B
2018/165
See application file for complete search history.

(56) References Cited

U.S. PATENT DOCUMENTS

| | | | |
|---|---|---|---|
| 5,391,199 A | 2/1995 | Ben-Haim |
| 5,443,489 A | 8/1995 | Ben-Haim |
| 5,558,091 A | 9/1996 | Acker et al. |

(Continued)

FOREIGN PATENT DOCUMENTS

WO        2021202052 A1    10/2021

OTHER PUBLICATIONS

Extended European Search Report received for European Application No. 24219659.0, mailed on Apr. 11, 2025, 9 pages.

*Primary Examiner* — Michael F Peffley

(57) ABSTRACT

Systems and methods for unipolar Pulse-Field Ablation (PFA) are disclosed for reducing spasm and/or other adverse nerves stimulation effects during delivery of PFA pulses. The system includes or is connected to one or more motion sensors to be placed at one or more regions of a patient's body for monitoring spasm thereat. The system includes a signal switch capable of selectively connecting a PFA energy generator to selected one or more of return electrode patches for delivery of PFA pulses and/or pacing signals through the selected electrode patches; and a processor that monitors motion sensed by the motion sensor(s) during delivery of the PFA pulses or pacing signals to identify nerve stimulation effects, such as spasm, to facilitate, based on the monitoring, selection of certain electrode patches by which the PFA pulses may be delivered without, or with reduced spasm or other adverse effects of excessive nerves stimulation.

23 Claims, 4 Drawing Sheets

(52) U.S. Cl.
CPC ............... *A61B 2018/00773* (2013.01); *A61B 2018/1465* (2013.01); *A61B 2018/1467* (2013.01); *A61B 2018/165* (2013.01)

(56) References Cited

U.S. PATENT DOCUMENTS

| | | | |
|---|---|---|---|
| 6,172,499 B1 | 1/2001 | Ashe | |
| 6,239,724 B1 | 5/2001 | Doron et al. | |
| 6,332,089 B1 | 12/2001 | Acker et al. | |
| 6,484,118 B1 | 11/2002 | Govari | |
| 6,618,612 B1 | 9/2003 | Acker et al. | |
| 6,690,963 B2 | 2/2004 | Ben-Haim et al. | |
| 6,788,967 B2 | 9/2004 | Ben-Haim et al. | |
| 6,892,091 B1 | 5/2005 | Ben-Haim et al. | |
| 7,536,218 B2 | 5/2009 | Govari et al. | |
| 7,736,357 B2 * | 6/2010 | Lee, Jr. .................. | A61B 18/16 606/34 |
| 7,756,576 B2 | 7/2010 | Levin | |
| 7,848,787 B2 | 12/2010 | Osadchy | |
| 7,869,865 B2 | 1/2011 | Govari et al. | |
| 8,100,898 B2 * | 1/2012 | Gregg ................. | A61B 18/1233 606/34 |
| 8,403,925 B2 * | 3/2013 | Miller ................ | A61B 18/1492 606/34 |
| 8,456,182 B2 | 6/2013 | Bar-Tal et al. | |
| 2009/0171344 A1 * | 7/2009 | Pontis ................ | A61B 18/1233 606/35 |
| 2013/0109994 A1 | 5/2013 | Cho et al. | |
| 2019/0038171 A1 * | 2/2019 | Howard ................... | A61B 5/24 |
| 2021/0228260 A1 * | 7/2021 | Canady, Jr. ........ | A61B 18/1206 |
| 2023/0051310 A1 | 2/2023 | Govari et al. | |
| 2023/0120856 A1 | 4/2023 | Govari et al. | |
| 2023/0190371 A1 * | 6/2023 | Govari .................. | A61B 18/16 606/41 |
| 2024/0293177 A1 * | 9/2024 | Dahlen .............. | A61B 18/1492 |
| 2025/0248757 A1 * | 8/2025 | Govari .............. | A61B 18/1206 |

* cited by examiner

Front-View                              Back-View

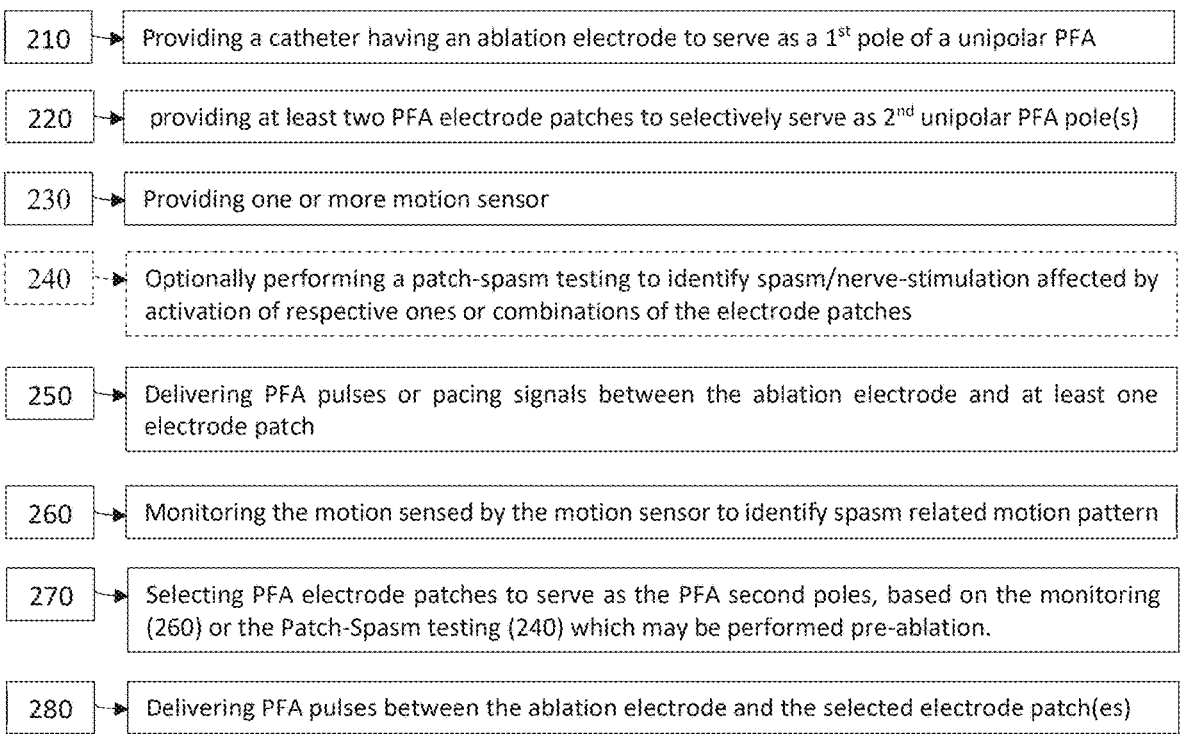

200 - A method for use in unipolar PFA

| 210 | Providing a catheter having an ablation electrode to serve as a 1$^{st}$ pole of a unipolar PFA |

| 220 | providing at least two PFA electrode patches to selectively serve as 2$^{nd}$ unipolar PFA pole(s) |

| 230 | Providing one or more motion sensor |

| 240 | Optionally performing a patch-spasm testing to identify spasm/nerve-stimulation affected by activation of respective ones or combinations of the electrode patches |

| 250 | Delivering PFA pulses or pacing signals between the ablation electrode and at least one electrode patch |

| 260 | Monitoring the motion sensed by the motion sensor to identify spasm related motion pattern |

| 270 | Selecting PFA electrode patches to serve as the PFA second poles, based on the monitoring (260) or the Patch-Spasm testing (240) which may be performed pre-ablation. |

| 280 | Delivering PFA pulses between the ablation electrode and the selected electrode patch(es) |

FIG. 3B

SYSTEM AND METHOD OF UNIPOLAR PFA

TECHNOLOGICAL FIELD

The present invention relates to medical systems, and in particular, but not exclusively, to cardiac ablation using irreversible electroporation (IRE) via unipolar pulsed field ablation (PFA).

BACKGROUND

Diagnosis and treatment of cardiac arrhythmias include mapping the electrical properties of heart tissue, especially the endocardium, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure, mapping followed by ablation, electrical activity at points within the heart is typically sensed and measured by advancing a catheter containing one or more electrical sensors into the heart, and acquiring data at a multiplicity of points. These data are then utilized to select the endocardial target areas at which the ablation is to be performed.

A typical ablation procedure involves the insertion of an ablation catheter having a one or more electrodes at its distal end into a heart chamber such that at least one of the electrodes is in electrical contact with a site of aberrant electrical activity therein, and operating that electrode with electrical signals affecting ablation of the sited having the aberrant electrical activity.

One ablation technique which is in common use in medical practice, is thermal ablation (also known as RF ablation). In this technique RF (radio frequency) current is applied through the tip electrode(s) of the ablating catheter, and current flows through the media that surrounds it, i.e., blood and tissue, between the tip electrode(s) and a reference electrode that is typically provided/taped on the skin of the patient or by means of a second catheter that is positioned in or near the heart. The distribution of current depends on the amount of ablation electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive.

Another ablation technique more recently in practice is Pulse Field Ablation (PFA) in which Irreversible electroporation (IRE) is applied via short electrical pulses referred to in the following PFA pulses, that generate high enough electrical fields (typically greater than 450 Volts per centimeter) to irreversibly damage the cells. Pulse Field Ablation (PFA) is generally a non-thermal IRE ablation which may be used in treating different types of tumors and other unwanted tissue without causing thermal damage to surrounding tissue. In this technique at least one relatively small ablation electrode is placed in proximity to target tissue, and short high voltage electric pulses are applied between the ablation electrode and another electrode, which may be (e.g. in bipolar PFA) another ablation electrode placed at the target tissue near the first ablation electrode, or (e.g. in unipolar PFA) a return electrode that is typically provided/taped on the skin of the patient or by means of a second catheter, at has a relatively large surface are to contact with the body so as not to affect ablation of tissues near the return electrode.

The short high voltage electrical pulses applied by PFA increase the resting transmembrane potential of the nearby cells, so that nanopores form in the plasma membrane. When the electricity applied to the tissue is above the electric field threshold of the target tissue, the cells become permanently permeable from the formation of nanopores. As a result, the cells are unable to repair the damage and die due to a loss of homeostasis and the cells typically die by apoptosis.

PFA may be used for cardiac ablation as an alternative to other cardiac ablation techniques, e.g., radio frequency (RF) cardiac ablation. As PFA is generally a low thermal technique, it reduces the risk of collateral cell damage that is present with the other techniques. e.g., in RF cardiac ablation.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 3A and 3B, schematically illustrate techniques to control of unipolar pulsed field ablation to reduce spasm or other adverse effects of nerve stimulation during an ablation treatment according to embodiments of the invention, in which: FIG. 3A is a block diagram exemplifying a configuration of a unipolar Pulse-Field Ablation control system 100; and FIG. 3B is a flow chart exemplifying the method 200 for unipolar PFA control.

DETAILED DESCRIPTION OF THE INVENTION

Figure 1:
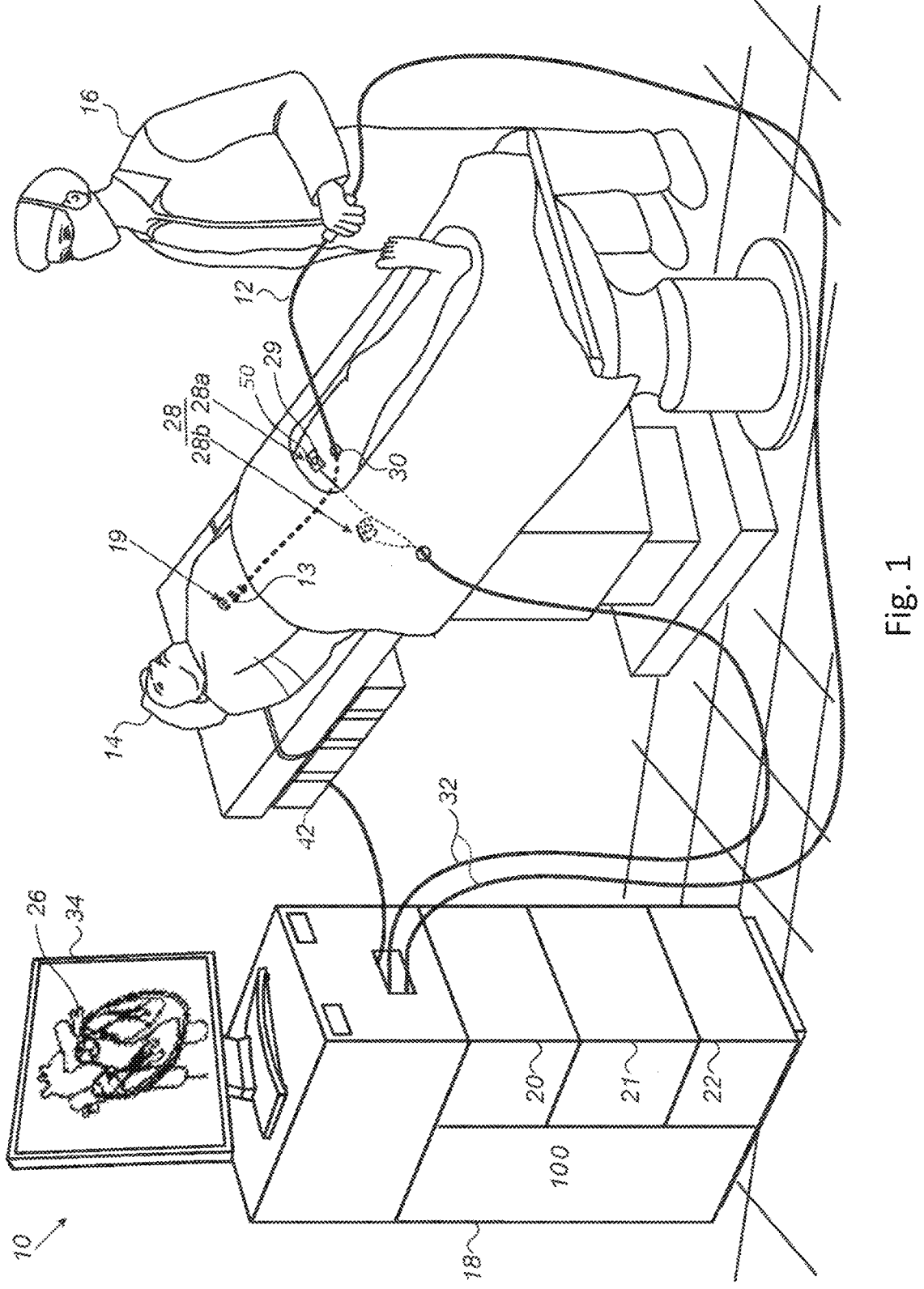
FIG. 1 is a schematic illustration of an ablation system 10 for pulse field tissue ablation with reduced spasm or other adverse effects of nerve stimulation in accordance with some embodiments of the present invention.

Pulsed field ablation (PFA) employs delivery of energy to a target tissue that is to be ablated via high voltage pulses generated by an ablation energy/signal generator. The high voltage pulses are typically delivered via electrodes electrically connected to a first and second poles of the ablation energy/signal generator and arranged coupled to the subject's body in a unipolar or bipolar fashion, whereby in bipolar PFA typically electrodes connected to both the $1^{st}$ and $2^{nd}$ poles are arranged/placed in close proximity to the target tissue to be ablated, and in unipolar PFA only electrode(s) that are connected one of the poles (hereinafter referred to as ablation electrode(s) and are considered without limitation to be connected to the $1^{st}$ pole) are placed in close proximity to the target tissue for affecting ablation thereof while electrode(s) connected to the other pole (herein after referred to as return electrode(s) and considered without limitation to be connected to the $2^{nd}$ pole) are typically coupled to the subject's skin/tissue remotely from the target tissue and are typically configured with larger surface area than the ablation electrode(s) so as not to affect ablation at the regions at which they are coupled to the subject.

In both types of PFA ablations, the energy flow through the subject's body between the electrodes that are connected to the $1^{st}$ and $2^{nd}$ poles of the ablation energy/signal generator, may affect stimulation of nerves, which may reside in the pathway of the ablation energy flow through the subject's body. This in turn may cause spasm of muscles associated with the stimulated nerves, whereby the term spasm is used herein to refer to an involuntary contraction of a muscles or group of muscles caused for instance by abnormal nerve stimulation during PFA ablation treatment. Such spasm may be accompanied by bursts of pain and discomfort to the subject, and in some cases may provide indication of a risk for causing permanent damage to the stimulated nerves.

For instance, when applying PFA ablation to a subject heart, the phrenic nerve may be inadvertently stimulated, which may be apparent by spasm of the diaphragm, and which in severe cases lead to damage of the phrenic nerve. PFA ablation, and specifically unipolar PFA, in which the return electrodes are often arranged at skin patches remote from the target tissue to be ablated, may also cause stimulation of other nerves and affect spasm of other muscles, such as skeletal muscles.

To this end, avoidance or reduction of spasm during PFA treatments is desired in order to reduce subject's discomfort during the treatment and also to avoid/reduce the risk for causing nerve damage. The technique of the present invention is designated to achieve these goals, and reduce or avoid spasm in unipolar PFA treatment. Indeed, in both unipolar and bipolar PFA treatments, certain spasm effects may be avoided or reduced by changing the location of the ablating electrodes (e.g. of the ablation catheter). This however actually typically entails moving from the designated target tissue, e.g. or ablating nearby tissues instead.

However, as recognized by the present invention, advantageously in unipolar PFA, certain spasm effects may be reduced or avoided without changing the target tissue/ location that is to be ablated, by instead changing the locations at which the return electrodes of the unipolar ablation are coupled to the body. This in turn may affect/ change the pathway of the ablation energy flow through the subject's body, and thereby change, reduce or eliminate certain nerve stimulation and of spasm associated therewith.

To this end, the present invention exploits these advantage of unipolar PFA treatment and provides methods and systems for reduction/elimination of spasm in unipolar PFA treatment via proper monitoring of spasm related effects when using PFA return electrodes at one or more locations, and proper selection of the return electrodes (e.g. according to their location on/in the subject's body) such that excessive nerve stimulation and/or its effects (e.g. spasm and/or nerve-damage) are reduced or eliminated.

Reference is initially made to FIG. 1, which is a schematic illustration of a system 10 for ablating tissue of a subject 14 while avoiding/reducing spasm or other effects of nerve stimulation, in accordance with some embodiments of the present invention. More specifically system 10 is configured and operable for carrying out Pulsed Field Ablation (PFA) also known as IRE ablation and specifically is adapted for performing unipolar PFA.

System 10 comprises an ablation catheter 12, comprising a distal tip 13 that includes an ablation electrode 19 of relatively small surface area adapted to contact a designated tissue region whose ablation is thought. Catheter 12 is inserted, by a physician 16, into subject 14. For example, catheter 12 may be inserted, via an insertion point 30, into vasculature of the subject, and the distal tip 13 thereof may then be navigated to a particular location within the subject's body (e.g. within the heart at which a target tissue to be ablated is located).

Typically, catheter 12 includes, at the distal end 13 thereof, a position sensor (not specifically shown in the figure) that provides data/signals indicative of the real-time position of the distal end 13 of the catheter (the term position herein the following should be understood as refereeing to a location and/or orientation relative to the subject's 14 body). Accordingly, the position of the of the ablation electrode 19 within (relative to) the subject's body/target-tissue, is trackable by the system 10, thus enabling the physician 16 to place the ablation electrode 19 at specific target tissue whose ablation is desired and apply the PFA at that location. It should be understood that in various embodiments the system may include/or be connectable to additional position sensors, which may be for instance arranged in other medical devices, and may be adapted to track the positions of these sensors as well.

In some embodiments the position sensor(s) are magnetic position sensors operating in conjunction with location pad 42 which includes a plurality of location signal transmitters (e.g., magnetic coils) that generate/transmit electro-magnetic location signals (e.g., magnetic fields) in a predefined working volume surrounding the patient. Real time position of the distal tip 13 of the catheter 12 may then be tracked relative to the patient's body based on the magnetic/electromagnetic location signals that are generated with location pad 42 and sensed by magnetic based position sensor. Details of the magnetic based position sensing technology are described in U.S. Pat. Nos. 5,5391,199; 5,443,489; 5,558,091; 6,172,499; 6,239,724; 6,332,089; 6,484,118; 6,618,612; 6,690,963; 6,788,967; 6,892,091, which are incorporated herein by reference.

Alternatively, or additionally, in some embodiments the position of the distal end 13 of the catheter 12 may be tracked/determined by impedance-based location tracking. In such embodiments the position sensor on the distal end 13 may include an ECG sensor(s)/electrode(s), and impedance-based location tracking may be employed to determine their positions utilizing impedance-based tracking techniques. For impedance-based tracking, electrical current is directed to electrodes (e.g., ECG electrodes in case such are included at/on the distal end portion 13). The electrical current is then sensed at skin ECG electrodes (not specifically shown) so that the location of the ECG sensor(s)/electrode(s) on the distal end portion 13 can be triangulated via the skin ECG electrodes. Details of the impedance-based location tracking technology are described in U.S. Pat. Nos. 7,536,218; 7,756, 576; 7,848,787; 7,869,865; and 8,456,182.

According to embodiments of the present invention the system 10 is adapted to perform a unipolar PFA ablation, by delivering/feeding PFA signals to pass between the ablation electrode 19 on the catheter's 12 distal end 13, and at least one electrode patch, e.g., 28a, placed on the subject's 14 body/skin. To this end, the system 10 further includes, or is associated with, one or more electrode patches 28, each including at least one electrode 29 (also referred to herein as return electrode) to be coupled to the body/skin of subject 14). The return electrode 29 has typically a relatively large surface/contact area, relative to that of the ablation electrode 19, such that during ablation, when electrical PFA pulses are applied in between the ablation electrode 19 and the return electrode 29, IRE is being substantially permanently affected at the ablation electrode 19, which has the substantially smaller surface area, while substantially not affected, or not permanently, near the return electrode 29 of the patch(s) 28 participating in the ablation.

In the particular example shown in FIG. 1, system 10 comprises two ablation electrode patches 28 *a* and 28 *b* that are coupled to the skin of the subjects, for instance near at his hips/thighs/back/chest/leg. Notwithstanding, the above, it is noted that, in general, system 10 may include any suitable number of electrode patches 28 (at least one), coupled to the subject in any suitable arrangement.

Generally, according to embodiments of the present invention, the system 10 includes or is associated with one or more motion sensors 50 that are may be arranged to sense motion of the patient's tissue/skin at certain locations of interest (for instance arrange near certain muscles that are associated with nerves that may be expected to be optionally stimulated by the ablation treatment) and adapted provide signals indicative this motion.

For instance, in some embodiments one or more accelerometers 50 (a single one is illustrated in the none-limiting example of FIG. 1) are arranged in/on or nearby respective one or more electrode patches 28. Indeed, as often the pathways through the body of the ablation energy delivered in between the ablation electrode 19 and the electrode patch(es) e.g., 28*a* that is used in certain tissue ablation, it is often expected that nerves near the electrode patch(es) will be stimulated and thereby affect spasm of muscles near the participating electrode patch e.g., 28*a*. Therefore, in some embodiments the one or more accelerometers 50 include at least one accelerometer 50 that is arranged near one (or more) of the electrode patch(es) 28. For instance, in some embodiments at least one electrode patch e.g. 28*a* of the electrode patches 28 used in the ablation may include a respective motion sensor that is adapted to sense motion (e.g. movement/acceleration) of the patient's tissue/skin near the patch.

Figure 2A:
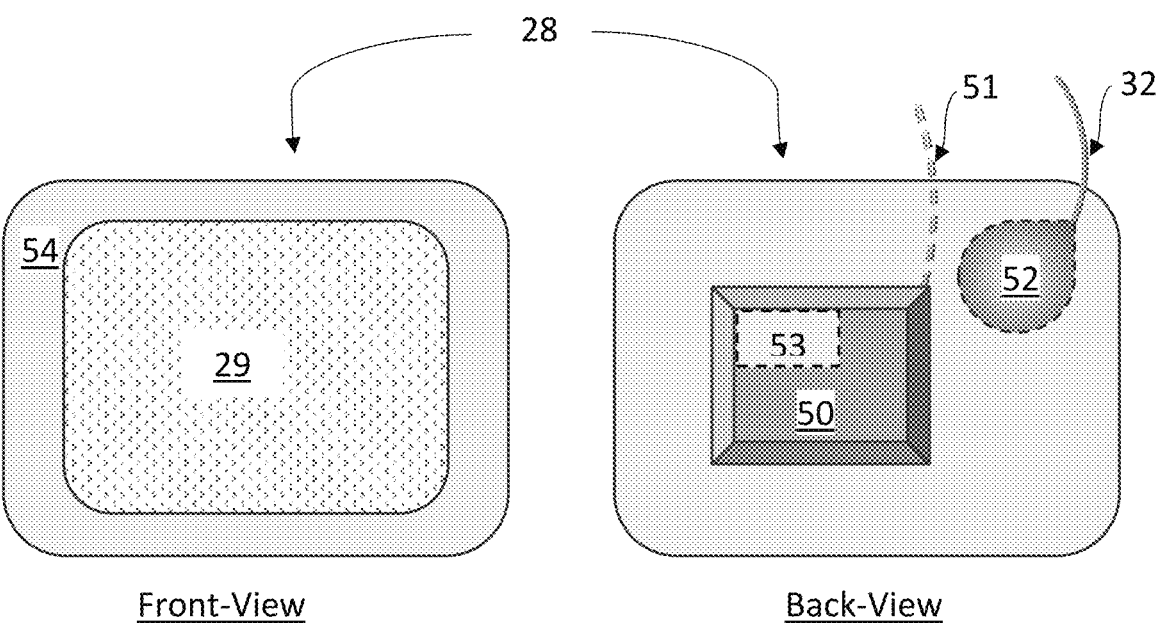
FIGS. 2A and 2B. are schematic illustrations of an electrode patch for unipolar pulsed field ablation which are adapted to incorporate a motion sensor according to embodiments of the present invention.
Figure 2B:
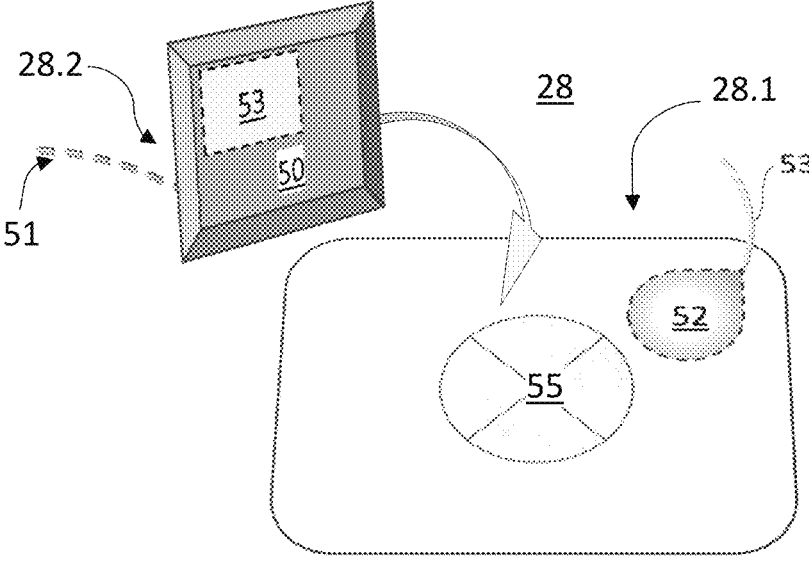

Embodiments of electrode patches 28 which include or can be coupled with motion sensors and configured and operable according to embodiments of the present invention are illustrated schematically in FIGS. 2A and 2B. FIG. 2A illustrates front and back views of an electrode patch 28, and FIG. 2B is a perspective view of an electrode patch 28 including disposable and reusable parts, 28.1 and 28.2 respectively. As illustrated in these figures, an electrode patch 28 adapted to incorporate motion sensor 50 includes:

an electrode 29 (also referred to herein as return electrode) associated with ablation signal wire/cable 32 that is connected or connectable thereto via optional connector 52 for supply of ablation signals to the return electrode 29. The return electrode 29 is configured with a relatively large surface area (e.g. few times larger than that of the ablation electrode 19) so as to avoid tissue ablation in the vicinity thereof.

an adherence patch (skin patch) 54 adapted to adhere to a skin/tissue of the subject to facilitate electrical coupling of the return electrode 29 to the skin/tissue; and a motion sensor 50 for sensing motion, such as accelerations/vibration of the patch 28. The motion sensor 50 may include for example one or more inertial sensors (e.g. inertial measurement unit (IMU); and/or accelerometer and/or one or more gyros), and/or position sensor, operable at with sufficient measurement frequency (time resolution), e.g. in the order of 10 KHz or above for instance 32 KHz to facilitate detection of spasm. In some embodiments the motion sensor 50 is associated with, or includes, an optional wired signal cable 51 adapted to communicate measured motion signals measured by the sensor 50 to the system 10, and optionally providing power supply to the sensor 50. Alternatively, in some embodiments the motion sensor 50 is configured as a wireless sensor (e.g. battery operated) and includes an optional wireless communication utility 53, such as WIFI or Bluetooth network adapter, capable of wireless data/signal connection with the system 10 and adapted to communicate the motion signals measured by the sensor 50 to the system 10.

It should be noted that the electrode patch 28 shown in FIG. 2A may be disposable or non-disposable patch in its entirety, or partly disposable including a disposable part and a non-disposable/reusable part. FIG. 2B illustrates an example of an electrode patch 28 that includes a disposable part 28.1 and a reusable part 28.2. The disposable and reusable parts, 28.1 and 28.2, are mechanically connectable/attachable to each other via an attachment element/assembly 55. The attachment element/assembly 55 may include for instance: a pocket element (e.g., pocket in the disposable part 28.1 capable of containing/holding the reusable part 28.2); and/or a two-part, Snap-On or Velcro, assembly arranged in the disposable and reusable parts respectively 28.1 and 28.2, and/or any other attachment mechanisms as may be suitable for mechanically attaching the disposable and reusable parts 28.1 and 28.2 to one another. In the particular non-limiting example of FIG. 2B, the disposable part 28.1 includes the return electrode 29 and the adherence patch (skin patch) 54 which are brought in contact with the subject's skin/tissue, as well as optionally the attachment element/assembly 55 or part thereof, the reusable part 28.2 includes typically relatively costly electronic components (e.g. which are generally not brought to contact with the subject) including in this example the motion sensor 50 (e.g. along with its associated wired or wireless communication utilities 51/53), and optionally the attachment element/assembly 55 or part thereof (not specifically shown on the reusable part 28.2 in the figure from the perspective it is illustrated there).

With reference made back to FIG. 1, it should be understood that the use of electrode patches 28 incorporating motion sensor(s) 50 therewith, as illustrated in FIGS. 2A and 2B is optional, and in various implementations, one or more, or all, of the motion sensors 50 that are incorporated with the system 10 may/or may not be incorporated within respective electrode patches 28, and may be arranged for example at spaced apart locations on the subjects skin/tissues separately from the electrode patches 28.

The system 10 is adapted to monitor the motion signals obtained from the motion sensor(s) 50 during or following the provision of an ablation PFA pulses or pacing signals between the ablation electrode 19 and one or more (selectively) participating patch(es) e.g. 28*a* of the patches 28 and process these motion signals, to determine whether spasm, such as spasm of skeletal muscle(s), is affected by the delivery of the PFA pulses or pacing signals between the participating patch(es) e.g. 28*a* and the ablation electrode 19.

The system 10 includes a console 18 including one or more units that facilitate performance of the techniques described herein. The ablation electrode 19 of the catheter 12 as well as the return electrodes 29 of the electrode patches 28 are typically connected to the console 18 of the system, via cables 32 and electrical interface(s) (such a ports or sockets). The motion sensor(s) 50 are typically connected, wirelessly or by wired connection (not specifically shown in FIG. 1) to the console 18 for providing data indicative of the motion sensed thereby, to the console 18. Additionally position sensor(s) (43 in FIG. 3A) typically located on the distal tip 13 of the catheter 12 (not specifically shown) may also be connected to the console 18 (e.g. by cables 32) to provide thereto position data/signals indicative of the real-time position of the distal end 13 of the catheter, and particularly of the ablation electrode 19 thereof.

Console 18 includes an PFA energy generator 22, configured to generate the electric PFA pulses, that are to be traversed during ablation between the ablation electrode 19 of the catheter 12 and at least one return electrode 29 of the electrode patches 28 via the subject's tissue, to thereby affect ablation of tissues located near the ablation electrode 19. Optionally also the PFA energy generator 22 is also adapted to generate pacing currents/signals that can be directed to pass in similar manner as the electric PFA pulses but without affecting ablation.

Additionally, console 18 typically also includes/implements a position tracking system 21 that processes the position data/signals obtained from the position sensor that may be furnished on medical devices connected to the system 10 to determine their position relative-to/within the patient's body. Specifically, as indicated above the ablation catheter 12 typically includes such a position sensor (not specifically shown in FIG. 1; 43 in FIG. 3A), and the position tracking system 21 operates to determine its location, and particularly the location of the ablation electrode 19 thereof relative to the patient's body (e.g. its specific location in/on the patient's heart), and to provide indication of the same to the physician 16 applying the ablation treatment.

According to embodiments of the present invention, console 18 typically includes an ablation control system 100 that is connected to the ablation energy generator 22 and is adapted to monitor spasm occurring during PFA ablation treatment, in particular unipolar ablation, or during delivery of pacing signals prior to actual ablation. System 100 is adapted to process motions signals/data received from the motion sensor(s) 50 (which may be furnished on one or more of the electrode patches 28 and/or at other locations on the patient's body), to determine whether the motion sensed by the motion sensor(s) 50 in response to PFA/pacing signal delivery via activation of each certain electrode patch(es) e.g. 28*a*, 28*b*, is indicative of muscle spasm (the term activation herein is used to designate connection of the electrode patch to the second pole of the ablation energy generator 22). Accordingly, the system 100 may determine/associate the activation of each certain patch, e.g. 28*a*, 28*b* with spasm affected or not in the vicinity of each of the motion sensor(s) 50. Based on the association between activation of each of one or more of the electrode patches 28 and affected spasm at different locations at which the motion sensors are furnished, the system facilitates automatic and/or manual selection of one or more of the electrode patches 28 to be activated during ablation (e.g. during ablation of specific target tissue(s) or throughout the procedure) in a manner that avoids/reduces the effects of spasm.

Indeed, in some embodiments/implementations of the invention, one or more of the motion sensor(s) 50 may be fitted on or near respective certain one or more of the electrode patches 28. In this case a motion sensor 50 fitted on/near a certain electrode path 28 is referred to herein as being associated with that patch 50. An underlaying rational of this arrangement is that the pathways of energy flow through the body between the ablation electrode 19 serving as the first pole and an activated electrode patch such as 28*a* serving a second pole, is expected to be typically concentrated near the electrode patch 28*a*, and thus spasm, if occurs, may likely occur at the region near the electrode patch 28*a*. Therefore fitting at least one, or all, of the motion sensor(s) 50 on respective patches 28, enables monitoring of the occurrence of spasm near those patches and applying proper selection of electrode patches to activate, so as to reduce or avoid spasm near the activated patches. Moreover, fitting one or more motion sensors on the electrode patches may reduce the time and complexity of the preparation to the ablation procedure.

Alternatively or additionally, in some embodiments/implementations of the invention, one or more of the motion sensor(s) 50 may be arranged at/near regions of interest (ROIs) on the patient's body (skin/tissue), at which spasm may be affected by the ablation due to stimulation of nerves nearby (not necessarily at regions proximal to the electrode locations of the patches 28 as the latter should typically be preferably located remotely from nerves that can be stimulated by the PFA ablation pulses). This enables monitoring of the occurrence of spasm at those ROIs and applying proper selection of electrode patches to activate so as to reduce or avoid spasm at those ROIs.

To this end, the ablation control system 100 may be adapted to monitor the motion signals obtain from the motion sensor(s) 50 following delivery of a pacing or PFA signal with via one or more of the electrode patches 28 activated as second pole(s), activation to identify occurrence of muscle spasm near the sensor(s) 50 in association with the activated electrode patches 28. This monitoring, which may be carried out one or more times with different activated electrode patches 28 or different combinations of patch(es), e.g. in a preliminary/preparation stage of the procedure or during actual ablation treatment, serves to facilitate selection of an electrode patch (e.g. 28*b*) or optionally a combination of the electrode patches 28 to be activated for serving as the ablation's second pole, such that nerve stimulation and/or spasm associated therewith is avoided/reduced, or at least being limited to regions at which it might affect less damage or discomfort (e.g. away from ROIs at which spasm should be avoided).

In various implementations the selection of the electrode patch(es) 28 that are to be operated as the ablation's second pole, may be performed automatically by the ablation system 100, or manually, whereby the ablation control system 100 provide indication of the occurrence of spasm to physician 16, and responsively obtains operational instructions indicative of the electrode patch(es) 28 which are to be selected for activation.

To this end, in some embodiments, typically, the system 10 further includes a user interface (UI) 34 typically including a display and user input devices (e.g. joystick, mouse, keyboard and/or other device(s)), adapted to facilitate performance of the ablation procedure/treatment by displaying relevant information to physician 16 and receiving therefrom respective instructions/inputs for implementing the ablation procedure.

For example, the ablation system 100 may cause the UI 34 to display indication of patch electrodes 28 whose activation as the second ablation pole might be affecting spasm or not affecting, to physician 16, and operate to receive from the UI 34 in response, data indicative of selected patch electrode(s) 28 to activate as the second ablation pole. Moreover, system 10 (e.g. the position tracking system 21 thereof) may be adapted to cause UI 34 to display the location/position of the catheter 12, e.g., by superimposing an icon representing the distal tip 13 of the catheter, or the ablation electrode 19 thereof, over an image of the subject's anatomy (in this particular example the heart).

Typically, system 10 includes one or more processors 20 by which certain functions of the system and/or its subsystems 100, 21 and 22 are implemented. In general, processor 20 may be embodied as a single processor, or as a cooperatively networked or clustered set of processors. In some embodiments, processor(s) 20 is implemented solely in hardware, e.g., using one or more Application-Specific Integrated Circuits (ASICs) or Field-Programmable Gate Arrays (FPGAs), analog and/or digital signal processing circuits and the like. In other embodiments, the processor is at least partly implemented in software. For example, processor 20 may be implemented with a programmed digital computing device comprising a central processing unit (CPU), random access memory (RAM), non-volatile secondary storage, such as a hard drive or CD ROM drive, network interfaces, and/or peripheral devices. Program code, including software programs, and/or data are loaded into the RAM for execution and processing by the CPU and results are generated for display, output, transmittal, or storage, as is known in the art. The program code and/or data may be downloaded to the computer in electronic form, over a network, for example, or it may, alternatively or additionally, be provided and/or stored on non-transitory tangible media, such as magnetic, optical, or electronic memory. Such program code and/or data, when provided to the processor, produce a machine or special-purpose computer, configured to perform the tasks described herein.

Figure 3A:
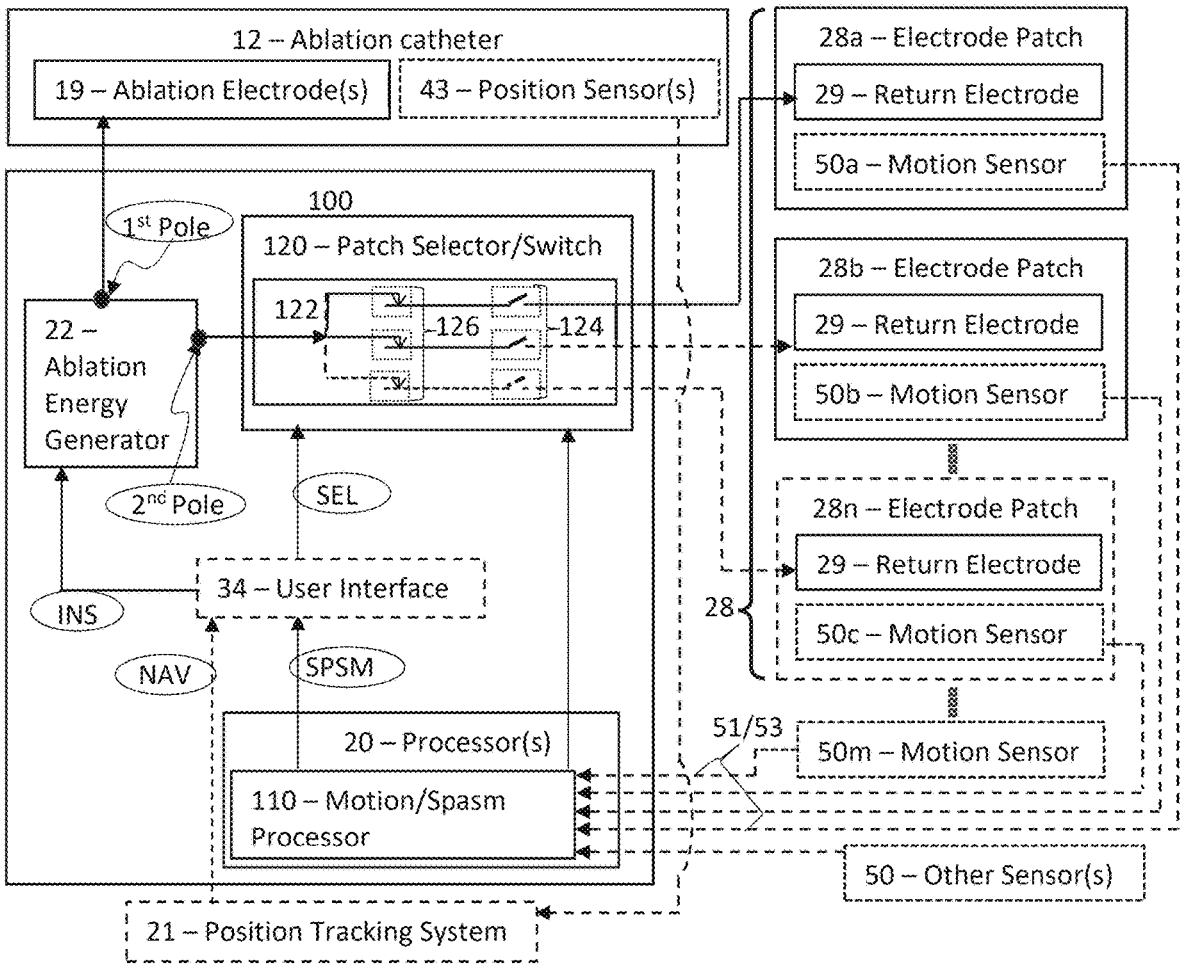

Reference is now made together to FIGS. 3A and 3B, schematically illustrating in more details the ablation control system 100 and method 200 according to some embodiments of the present invention. The system 100 and method 200 are adapted to monitor occurrence of spasm during and unipolar PFA ablation treatment, or in preparation thereto (where pacing signals may be delivered), and facilitate automatic or manual selection of electrode patches 28 to avoid/reduce the effects of spasm or of nerve stimulation causing the spasm. More specifically, FIG. 3A is a block diagram exemplifying a configuration of the ablation control system 100 for control of unipolar Pulse-Field Ablation (PFA); and FIG. 3B is a flow chart exemplifying the method 200 for unipolar PFA, which may be for instance implemented by system 100.

As illustrated the system 100 is connected or connectable to an ablation catheter 12 having at least one ablation electrode 19 at a distal end 13 thereof. System 100 is also connected or connectable to a plurality of electrode patches 28 (at least two: 28a and 28b and optionally additional ones e.g., 28n) whereby each electrode patch includes at least one return electrode 29 that is suitable for use in unipolar PFA ablation.

The system is further connected or connectable to one or more motion sensors 50 (50a to 50m exemplified in the figure). For instance, as illustrated in FIG. 3A, the motion sensor(s) 50, may optionally include motion sensors such as 50a, 50b and/or 50c that may be associated with one or more of the electrode patches 28 (i.e. arranged/included on, or in vicinity of, respective ones of the electrode patches 28, such as on patches 28a, 28b and/or 28n shown in the figure). Alternatively, or additionally, as also indicated above, the motion sensor(s) 50, may optionally include motion sensors, such as 50m, associated with certain regions of interest (ROIs) of the patient's body—i.e. being arrange near/on these ROIs, which may be strategic locations at which it spasm or other effects of nerve stimulation should preferably monitored. For instance, ROIs at which motion sensors may be placed, can include a region/skin-region in the vicinity of the patient's diaphragm, to monitor diaphragm spasm associated with phrenic nerve stimulation, and/or region/skin-region on the patient's chest or otherwise near his heart in order to monitor changes in heartbeat, which may be associated with stimulation of the vagal nerve.

Moreover, the system 100 may be further connected to additional sensors 60, such as ECG sensors/electrodes by which certain effects of nerve stimulation due to the ablation treatment, such as changes in electrical activation of the heart due to vagal nerve stimulation can be identified.

The system includes an ablation energy generator 22, specifically pulsed-field ablation (PFA) energy generator, having a $1^{st}$ and $2^{nd}$ electric poles via which the ablation energy generator 22 is configured and operable to deliver one or more PFA pulses or pacing signals. Typically, the at least the first electric pole is electrically connected to the ablation electrode(s) 19 of the catheter 12 to enable ablation of tissue proximal thereto. For unipolar ablation procedures, the second electric pole of the ablation energy generator 22 should be electrically connected to at least one of the electrode patches 28.

The system 100 further includes a patch switch/selector 120 being connected/connectable between the second electric pole of the PFA energy generator 22 and one or more of the electrode patches 28. Specifically, the patch switch/selector 120 is adapted selective connection with the return electrodes 29 of the plurality of electrode patches 28, and operable to selectively deliver the PFA pulses or pacing signals generated by the PFA energy generator 22 from the second pole thereof and return electrode(s) of a selected at least one of the electrode patches 28. To this end, the patch switch/selector 120 may include or be implemented for instance by an electronic signal distribution circuit 122 optionally including one or more switches 124 and/or optionally one or more current/voltage controllers 126 by which the delivery of the PFA pulses or pacing signals to the electrode patches 28 may be controlled.

Processor(s) 20 including/implementing a spasm/motion processing capability 110 (herein after also referred to without loss of generality as spasm/motion processor) that is connected directly or indirectly, wirelessly or by wired connection, to the one or more motion sensors 50. The spasm motion processor 110 is adapted to monitor the motion indicated by signals obtained from the motion sensor(s) 50 connected thereto, and identify spasm related motion patterns in vicinity thereof. Moreover, it should be noted that in some embodiments the spasm/motion processor 110 may be further adapted for connection with additional sensors 60 (such as ECG sensor(s)/electrode(s)) for sensing other effects of certain nerve stimulation which might occur during an ablation treatment (such as changes in heart activation due to stimulation of the vagal nerve).

Specifically for example, following delivery of one or more PFA pulses or pacing signals to one or more of the electrode patches 28, the spasm motion processor 110 obtains and processes the signals received from one or more of the motion sensors 50 to determine whether the motions sensed thereby manifests a spasm related motion pattern. The spasm motion processor 110 may not necessarily monitor all of the motion sensors at each activation of PFA pulses or pacing signals, and may for example only monitor the motion sensors associated with the active electrode patches, if any (which serve as the $2^{nd}$ pole during the activation), and/or motion sensors associated with certain ROIs as indicated above.

In some embodiments, the system 100 may be adapted to perform a patch pre-ablation screening procedure (also referred to herein as patch-spasm testing), to determine an association, between the activation of certain electrode patches 28 or combination of patches, and spasm affected by such activation at different body location at which the motion sensors are placed, and/or with other effects indicative of stimulation of nerves which may be caused during the PFA treatment. Such pre-ablation screening procedure may be performed for example at a preliminary stage or during the PFA treatment, and may include one or more cycles each including: delivery of the PFA pulses or pacing signals with a different electrode patch or combination of patches 28 being activated at different cycle; and monitoring of spasm related motion pattern sensed by the motion sensor(s) 50, or other spasm effects, e.g. sensed by other sensor(s) 60, during each cycle. Accordingly, an association between the activation of certain electrode patches 28 and stimulation of certain nerves may be determined, facilitating informed selection of certain of the electrode patches 28 to be further used during the ablation treatment, in order to avoid/reduce excessive nerve stimulation, and/or other effects such as spasm manifested by such stimulation.

Optionally in some embodiments of the present invention, based on the monitoring indicated above, and/or based on the pre-ablation screening procedure, the spasm motion processor 110 may automatically select one or more electrode patches 28 to serve as the second poles for the entire unipolar PFA treatment, and/or for certain activations of the PFA pulses during the PFA treatment. Accordingly, the spasm motion processor 110 operates the patch selector/switch for electrically connecting the second pole of the ablation energy generator 22 to the return electrodes 29 of the selected electrode patch(es) such that the PFA pulses or pacing signals further generated by generator 22 will be delivered to the patient's body via the selected electrode patch(es)—which therefore function as the active patches via which the PFA pulses or pacing signals are delivered.

Alternatively, or additionally, in some embodiments system 100 comprises or is associated with user interface 34. The spasm motion processor 110 may be configured and operable to issue indication about the identified spasm related motion pattern to the physician 16, upon detection of spasm related motion by the monitoring indicated above, which may be carried out throughout the ablation treatment or at selected time thereof. Yet alternatively, or additionally, the spasm motion processor 110 may be configured and operable for implementing the patch pre-ablation screening procedure described above, e.g. automatically and/or in response to user's instructions (e.g. from physician 16), and issue indication about the spasm related motion pattern identified thereby, and/or about the association between the activation of certain electrode patches 28 and stimulation of certain nerves determined by said pre-ablation screening procedure. The indication about the identified spasm related motion pattern, and/or about the association between activated patches or combination of patches therewith, may be issued to the physician 16 for example via the user interface 34. Responsive to such indication, the spasm motion processor 110 may be adapted to obtain, e.g., via the user interface 34, user instructions SEL for a desired the patch selection—e.g., the specific one or more selected electrode patches preferred by the physician 16 for use as the active patches (i.e., as the second pole) during the unipolar ablation treatment, or for certain PFA pulse activation(s) (e.g., for ablation of certain region).

In this regard, it should be noted that in some embodiments of the invention, the motion sensors 50, or any one or more of them, may also include, or be implemented by position sensor(s), trackable by the position tracking system 21, which may be included in system 100 and/or in system 10 illustrated in FIG. 1 and registered to the patient's body (e.g. based on the registration of the location pads 42 illustrated in FIG. 1 with the body). In such embodiments the indication about the identified spasm related motion pattern(s) sensed by any of the motion sensors 50, and/or about the association between activated patches and stimulated nerves, may be presented in a display of the UI 34 (e.g. to physician 16) on top of an anatomical map illustrating the organs or nerves (e.g. ROIs), in the vicinity of which spasm related motion pattern was sensed by one or more of the sensor(s).

Accordingly, in various embodiments the system 100 determines the selected one or more electrode patches SEL either automatically and/or based on the user's instructions (i.e. manually) and may operate to deliver further PFA pulses or pacing signals via the return electrodes of the selected one or more electrode patches so as to avoid or reduce spasm, such spasm of skeletal muscles spasm near the electrode patches used in the unipolar ablation, and/or to avoid or reduce spasm at other ROIs and/or other unwanted effects of nerve stimulation during the PFA treatment.

The operation of the system 100 is exemplified in the following with more details with reference to FIG. 3B that illustrates a method 200 for unipolar PFA, which is implemented by system 100 according to some embodiments of the invention. In operations 210 to 230 an ablation catheter 12 having at least one ablation electrode 19 serving as a first pole of the unipolar PFA and a plurality (at least two) electrode patches 28 having return electrodes 29 suitable for serving as one or more second pole(s) of the unipolar PFA are provided, together with one or more motion sensors 50 to be at various ROIs of the patient's body or near/on one or more of the electrode patches 28.

Optionally, in some embodiments, an association between the motion sensors 50 and their associated electrode patches 28 and/or associated ROIs may be registered with the FPA system 100 (e.g. by the motion/spasm processor 110). In various embodiments such registration may be performed manually (by an operator/user of the system), or automatically for example based on registration signals communicated from the respective patch or motion sensor associated therewith once coupling between them may be detected e.g. by a coupling detector (which may be included on either one of the electrode patches and/or motion sensors—not specifically shown), and/or based on position sensors 43 in communication with the position tracking system 21 (e.g. by which the motion sensor(s) may be implemented or which may include with motion sensors).

In some implementations not all the electrode patches 28 are permanently fitted with, or include motion sensors 50 coupled thereto. For example, one motion sensor may 50 may be furnished, or moved-between, different electrode patches 28 during the PFA treatment, e.g. in accordance with the physician's 16 preferences to monitor occurrence of spasm near the selected/activated electrode patch(es) e.g. 28a that is/are currently to be used as second pole of the PFA treatment. Accordingly, in such implementations the system 100 may facilitate to perform the registration between the motion sensor(s) 50 and its associated electrode patch (e.g. 28a) or the ROI at which it resides, dynamically during the operation.

Thus, once the electrode patches 28 are set up, e.g. at one or more locations on the patients tissue/skin and the catheter 12 with the ablation electrode 19 at its distal tip is brought/navigated to proper tissue location at which ablation may be desired (e.g. a specific location in the patient's heart), operations 260 to 280 as described in more details below, may be carried out to determine selected one or more of the electrode patches 28 which when activated as second pole(s) during the PFA ablation, prevent or reduce excessive nerve stimulation, or its effects (e.g. spasm).

In this regard, optionally, in some embodiments pre-ablation screening operation 240 may be carried out, automatically by the system 100, and/or in response to instructions INS (e.g. from the physician's 16 via the UI 34). In the pre-ablation screening operation, operations 250 and 260 described below may be repeated one or more times/cycles for: delivery of pacing signals and/or PFA pulses (e.g. similarly as described below with reference to operation 250), with activation of different electrode patch or combination of the electrode patches 28 as the second pole(s) at each cycle, while monitoring the spasm or other effects resulting from excessive nerve stimulation in association with the activated patch electrode(s) (e.g. in a manner similar to the described below with reference to operation 260). Accordingly, an association between activation of certain selections of patch electrodes 28, and spasm/nerve-stimulation affected by such selections, is determined. This association may then be used of automatic and/or manual selection of a one or more selected patches to be activated during the ablation treatment, or during ablation of specific tissue, in a manner similar to the described below with reference o operation 270.

Alternatively, pre-ablation screening operation 240 per-se, may not be implemented, or skipped. Responsive to instructions INS from the physician/operator 16 (e.g., via UI 34), the system 100 may operate for delivery of pacing signals and/or PFA pulses between the ablation electrode 19 and return electrode(s) 29 of a certain at least one selected patch, e.g. 28a, and method operations 250 to 260 may be performed by system 100 responsive to the issuance of such instructions. In operation 250 one or more PFA pulses or pacing signals may be delivered by system 100 (e.g. by the ablation energy generator 22 and the patch selector/switch 120) between the ablation electrode 19 of the catheter 12 (which serves as the first pole of the unipolar PFA) and the return electrode(s) 29 of the selected one or more electrode patches, e.g. 28a (which serve as the second pole of the unipolar PFA). During and/or following the delivery of the PFA pulses or pacing signals, operation 260 is performed to monitor the motion sensed by the motion sensors 50 (e.g., for instance to monitor at least those motion sensor 50 which are associated with selected/activated electrode patch(es) as well as motion sensor(s) 50 and/or the other optional sensors 60 placed at specific ROIs of the subject/patient). The signals/data obtained from these motion sensors are processed (e.g., by the motion/spasm processor 110) to identify spasm related motion patterns in vicinity of the electrode patch(es) and/or ROIs. Additionally, the signals/data obtain from other optional sensors 60, such as ECG sensors indicated above, may also be processed to identify other possible effects of excessive nerve stimulation.

As indicated above, each motion sensor may be implemented by, or include, a position sensor and/or an inertial measurement unit, such as an accelerometer, and/or optionally also including gyro). The motion sensor(s) 50 may be adapted to provide the system 100, wirelessly or by wired connection, signals indicative of changes in velocity or acceleration of patient tissue near their associated electrode patch(es) 28 and/or ROIs (e.g. based on inertial measurements performed by their IMUs/accelerometers). In any case, as will be appreciated by those versed in the art, changes in any one of position, velocity of acceleration of the tissue(s) at the ROIs at which the motion sensor(s) are placed, or of patches associated therewith, may be derived from the signals obtained from the respective motion sensors in either of the implementations thereof indicated above.

Thus, the monitoring of the motion sensed by the motion sensors typically includes processing/filtering the signals obtained from respective motion sensors 50 to identify spasm related motion pattern therein. Such processing may involve for example applying a signal filter to the signals from respective motion sensors, and/or applying spectral analysis such as Fourier Transform (FFT) thereto, to identify frequency components therein, which are associated with spasm. For instance, a spasm related motion pattern is associated with changes in at least one of a position, velocity and acceleration of tissue near said electrode patch, and the processing/filtering may include spectral analysis of each motion sensor's signals to determine whether amplitudes of frequency components of these signals within that frequency range exceed a certain threshold—which is indicative of spasm related motion pattern near each specific motion sensor 50 being monitored. In this regard, a person of ordinary skill in the art will readily appreciate the characteristics of various spasm related motion pattern which may be identified by the system (their characteristic frequencies and amplitudes) and after knowing the present invention will readily appreciate how to implement such processing to identify these patterns.

Accordingly, based on the monitoring operation 260, once the processing of the motion sensed by a motion sensor associated with a certain electrode patch, such as 28a, reveals spasm related motion pattern occurring thereat, indication of the same may be provided to the physician 16 (e.g. via UI 34), or the system 100 may automatically switch to another electrode patch e.g. 28b for serving as the second pole of the unipolar PFA.

Alternatively, or additionally, as said above in some embodiments the monitoring operation 260 may be performed during a pre-ablation screening stage 240 with aim to determine conditions (e.g. the maximal/effective level/intensity) of pacing signals or PFA pulses which can be deliver through each of one or more of the electrode patches 28 without, or with reduced effects of nerve stimulation such as spasm. In such implementations operation 260 for monitoring the occurrence of spasm, may be performed concurrently/in-synchronization with varying intensity of the pacing signals/PFA pulses, to thereby reveal an intensity thereof, if any, at which spasm related motion pattern starts to appear near the respective motion sensor(s) 50. This may be performed for example by individually activating each electrode patch of the electrode patches 28 connected to the system 100, or to some of them, and the maximal/effective intensity not causing spasm may be recorded by the system 100 (e.g. by the motion/spasm processor 110) and/or presented to physician 16 (e.g. via UI 34), to aid in proper selection (automatic or manual) of at least one electrode patch (e.g. 28a) or a combination of the patches (e.g. 28a and 28b), which are to further serve/activate as second poles of the unipolar PFA ablation treatment.

Based on the spasm monitoring operation 260, in operation 270 of method 100, one or more electrode patches (e.g., 28a) of the plurality of electrode patches 28 are selected to serve/activate as the one or more second poles of the unipolar PFA. Typically, operation 270 may be performed following identification of the occurrence of spasm related motion pattern by the monitoring 260 during the conduction of an PFA treatment. Alternatively, or additionally, operation 270 may be performed after the pre-ablation screening 240 of the PFA treatment, during which the levels of the signals/ pulses deliverable through each patch without affecting spasm may be assessed.

As indicated above, in some implementations the operation 270 may be operated in "manual mode" in which the case the occurrence of spasm related motion SPSM or the conditions for affecting spasm or other adverse nerve stimulation effects by activation of one of more of the electrode patches are presented/indicated, e.g. by UI 34, in order to alert the physician 16 about occurrence of the spasm or other adverse effects, or to inform him about available options for patch selection and/or of PFA signal/pulse intensities, that are expected to affect/not-affect spasm. In such "manual mode" responsive to the such indication SPSM about the occurrence/conditions of spasm by activation of any one or more of the patches, the system 100 may receive input data/instructions INS which may indicate a selected one or more of the electrode patches 28 to serve/activate, individually or collectively, as the second pole(s) of the unipolar ablation. Optionally the input data/instructions INS may also indicate the intensity(ies)/level(s) or the relative portions of the PFA pulses that are to be transferred via each of the selected/activated electrode patches (e.g. in case more than one patch is selected).

Alternatively or additionally, as also indicated above, in some implementations the system 100 may be operated in "automatic mode", in which case following an the occurrence of spasm related motion detected by the monitoring 260, and/or based on the conditions for affecting spasm determined by the pre-ablation screening operation 240, the system 100, e.g. the motion/spasm processor 110, automatically selects the at least one or a combination of the electrode patches 28 which are to be further used as the second pole during the PFA treatment, and optionally also selects the proportion/level/intensity of the PFA pulses to by delivered via each of the selected patches. Typically, in this case, the system performs such selections based on the information acquired by the monitoring 250, with aim to avoid occurrence of spasm or other adverse nerve stimulation effects near the selected patches or the ROIs at which the motion sensors are furnished, and or reduce the duration and/or intensity of spasm or other adverse effects.

For instance, in some embodiments the system 100 may set as selected patches 28 only those one or more patches for which spasm/adverse-effects is not detected by the motion sensors 50 and/or by optional sensors 60, and/or detected with the lowest spasm amplitude/intensity. Alternatively, or additionally, based on the monitoring the system may equilibrate the intensities of the PFA signals through each selected patch to minimize the adverse effects of nerve-stimulation/ spasm. In this regard, a person of ordinary skill in the art after knowing the present invention, will readily appreciate various optimization methodologies and/or algorithms which may be implemented by the system 100 for selection of the electrode patch(es) to serve individually or collectively as the second PFA pole(s), and in the latter case, optionally optimization of the PFA pulse level/intensity to be delivered via each selected electrode patch, based on the information acquired by the monitoring 260, as described for example above.

Then, in operation 280 the system 100 operates to deliver the PFA pulses between the ablation electrode 19 of the catheter 12 and the selected electrode patch(es) (e.g. 28a). To achieve that the patch selector/switch 120 may be operated by the processor(s) 20 to activate the selected patches (e.g., electrically connects them to the second pole of the ablation energy generator 22 and substantially disconnect other electrode patches therefrom. This may be performed by controllably operating the one or more switches 124 and/or the current/voltage controllers 126 to perform such connection/disconnection. Additionally, optionally the patch selector/switch 120 (e.g., the current/voltage controllers 126 thereof) may be operated by the processor(s) 20 to adjust the level/portion of the PFA signal that will be delivered via each of the selected electrode patches, according to the maximal/effective levels/intensities of the PFA signal that is optionally determined therefore in operation 260.

EXAMPLES

Example 1. A method 200 for unipolar Pulse-Field Ablation (PFA), the method includes:
  providing an PFA system including: at least one catheter having at least one electrode serving as a first pole of the unipolar PFA and being furnished at a distal tip of the catheter to facilitate tissue ablation near said distal tip; and a plurality of at least two electrode patches for coupling at several locations on a subject's skin whereby each electrode patch includes at least one return electrode suitable for serving as a second pole of the unipolar PFA;
  providing at least one motion sensor for coupling respectively with, or near, at least one region of the subject's body; and
  delivering one or more PFA pulses or pacing signals between the at least one ablation electrode of the catheter serving as the first pole of the unipolar PFA and return electrodes of one or more electrode patches of the plurality of electrode patches set to serve as one or more second poles of the unipolar PFA during delivery of the one or more PFA pulses or pacing signals;
  monitoring the motion indicated by signals from the motion sensor following the delivery of the one or more PFA pulses or pacing signals to identify spasm related motion patterns in vicinity of the at least one motion sensor; and
  based on the monitoring, selecting certain one or more electrode patches of the plurality of electrode patches that are to further serve as the one or more second poles of the unipolar PFA, and delivering additional one or more PFA pulses or pacing signals via the return electrodes of the selected certain one or more electrode patches.

Example 2. The method according to example 1, wherein the at least one motion sensor includes a position sensor adapted to provide signals indicative of position changes of tissue near the at least one motion sensor respectively.

Example 3. The method according to example 1 or 2, wherein at least one motion sensor includes inertial measurement unit (IMU) adapted to provide the signals indicative of changes in velocity or acceleration of tissue near the at least one motion sensor respectively based on inertial measurements performed by the IMU.

Example 4. The method according to any one of examples 1 to 3, wherein the inertial measurement unit (IMU) includes at least one accelerometer.

Example 5. The method according to any one of examples 1 to 4, wherein the at least one motion sensor is a wireless motion sensor including a wireless communication utility capable of wirelessly communicating the signals to the PFA system.

Example 6. The method according to any one of examples 1 to 5, wherein the spasm related motion patterns is associated with changes in at least one of a position, velocity and acceleration of the tissue near the at least one motion sensor with frequencies within a certain frequency range, and wherein said monitoring of the motion includes processing the signals obtained from the motion sensor to determine whether amplitudes of frequency components of the signals within the frequency range exceeds a certain threshold.

Example 7. The method according to example 6, wherein the processing includes at least one of spectral analysis and filtering to identify the frequency components being within the frequency range.

Example 8. The method according to any one of examples 1 to 7, wherein selecting of the one or more electrode patches based on the monitoring, includes carrying out the following upon identification of the spasm related motion pattern by the monitoring:

issuing an indication about the identified spasm related motion pattern in association with one or more electrode patches in response to which activation as the one or more second poles, the spasm related motion pattern is identified; and responsive to the indication, obtaining user instructions for selection of the certain one or more electrode patches;

thereby delivering the one or more PFA pulses or pacing signals via the return electrodes of the selected one or more electrode patches in accordance with the user instructions.

Example 9. The method according to any one of examples 1 to 8, wherein the selecting of the one or more electrode patches is performed automatically based on the monitoring of the spasm related motion pattern sensed by the at least one motion sensors.

Example 10. The method according to any one of examples 1 to 9, wherein the providing of the at least one motion sensor includes at least one of the following:

provision of at least one motion sensor arranged at, or near, at least one respective electrode patch of the plurality of electrode patches; and provision of at least one motion sensor arranged at, or near, at least one region of interest of the subject's body at which spasm related motion pattern may occur due to nerve stimulation affected by the delivery of the PFA pulses or pacing signals.

Example 11. The method according to any one of examples 1 to 10, wherein this selecting of the one or more electrode patches based on the monitoring may include selection of more than one electrode patch to serve as the second pole.

Example 12. The method according to example 11, wherein in case more than one electrode patch are selected, the delivering of the PFA pulses or pacing signals includes adjusting the relative portions/intensities (e.g., voltages/currents) of the PFA pulses or pacing signals delivered through each of the selected electrode patches based on the monitoring, to thereby avoid or reduce spasm or other adverse effects of nerve stimulation near the selected electrode patches.

Example 13. The method according to any one of examples 1 to 12, wherein at least one of the electrode patches includes a coupling member suitable for attachment of one of the motion sensors thereto.

Example 14. The method according to any one of examples 1 to 13, wherein the PFA system is configured and operable to implement PFA treatment by delivering PFA pulses being high voltage direct current electrical signals, between the at least one electrode of the catheter and the selected at least one electrode patch of the plurality of electrode patches.

Example 15. A system for unipolar Pulse-Field Ablation (PFA), the system is connectable to: an ablation catheter having at least one ablation electrode at a distal end thereof; a plurality of at least two electrode patches each comprising at least one return electrode suitable for use in unipolar ablation; and at least one motion sensor for coupling respectively with, or near, at least one region of a subject's body;

the system includes a PFA energy generator adapted to deliver one or more PFA pulses or pacing signals between a first and second electric poles; whereby at least the first electric pole is electrically connectable directly or indirectly to the ablation electrode of the catheter serving as the first pole of the unipolar PFA, to enable ablation of tissue proximal to the ablation electrode; and wherein the system includes:

a signal switch being connected to the PFA energy generator, adapted for direct or indirect electric connection with return electrodes of the plurality of electrode patches, and operable for selective delivery of the PFA pulses or pacing signals between return electrodes of one or more selected electrode patches of the plurality of electrode patches that are set to serve as one or more second poles of the unipolar PFA; and at least one processor adapted to monitor the motion indicated by signals from the at least one motion sensor following delivery of the one or more PFA pulses or pacing signals to identify spasm related motion patterns in vicinity of the at least one motion sensor; based on the monitoring, select certain one or more electrode patches of the plurality of electrode patches to further serve as the one or more second poles; and operate the signal switch for connecting the PFA energy generator to return electrodes of the selected certain one or more electrode patches for further delivery of the one or more PFA pulses or pacing signals via the selected certain one or more electrode patches.

Example 16. The system according to example 15, wherein the at least one motion sensor includes at least one of a position sensor and an inertial measurement unit.

Example 17. The system according to example 15 or 16, wherein the motion sensor is a wireless motion sensor, and the system includes a wireless communication utility capable of wirelessly communicating with the motion sensor to obtain therefrom signals indicative of motion sensed thereby.

Example 18. The system according to any one of examples 15 to 17, wherein the spasm related motion pattern(s) are associated with changes in at least one of a position, velocity and acceleration of the tissue near the at least one motion sensor with frequencies within a certain frequency range, and wherein said monitoring includes processing the signals obtained from the at least one motion sensor to identify frequency components of that motion within that certain frequency range which are indicative of the spasm related motion pattern(s).

Example 19. The system according to any one of examples 15 to 18, wherein the selection of the certain one or more electrode patches includes carrying out the following upon identification of the spasm related motion pattern by the monitoring:

operating the user interface to issue an indication about the identified spasm related motion pattern; and responsive to the indication, obtaining via the user interface, instructions for selection of the certain one or more electrode patches;

thereby delivering the one or more PFA pulses or pacing signals via the return electrodes of the selected certain one or more electrode patches in accordance with the instructions.

Example 20. The system according to any one of examples 15 to 19, adapted for carrying out the selection of the certain one or more electrode patches, automatically based on the monitoring of the spasm related motion patterns sensed by the at least one motion sensor.

Example 21. The system according to any one of examples 15 to 20, adapted for connection with at least one motion sensor comprising at least one of the following:

at least one motion sensor arranged at, or near, at least one respective electrode patch of the plurality of electrode patches;

at least one motion sensor arranged at, or near, at least one region of interest of the subject's body at which spasm related motion pattern may occur due to nerve stimulation affected by the delivery of the PFA pulses or pacing signals.

Example 22. The system according to any one of examples 15 to 21, wherein the selection of the certain one or more electrode patches based on the monitoring may include selection of more than one electrode patch to serve as the second pole.

Example 23. The system according to example 22, wherein the signal switch is configured and operable to adjust relative portions (voltages/currents) of the PFA pulses or pacing signals being delivered through each of the selected electrode patches; and in case more than one electrode patch are selected, the processor adjusts the relative portions based on the monitoring, in order to avoid or reduce spasm sensed by the motion sensors.

Example 24. The system according to any one of examples 15 to 23, adapted to connect to at least one additional sensor capable of sensing additional effects of nerve stimulation due to said delivery of PFA pulses or pacing signals; and wherein the at least one processor is adapted to further monitor the signals obtained from the additional sensor and further select the certain one or more electrode patches further based on a monitoring of the signal from the additional sensor.

Example 25. A PFA electrode patch for use as a second non-ablating pole in unipolar PFA treatment. The PFA electrode patch includes: a return electrode being skin surface electrode adapted for coupling to a patient's skin over a surface area substantially larger than contact area of an ablation electrode used in the unipolar PFA treatment; an electrical connector for connecting the return electrode to PFA energy generator serving as an energy source of a PFA ablation system; and a coupling member adapted to couple at least one motion sensor to the PFA electrode patch, to facilitate identification of muscle spasm occurring during unipolar PFA treatment in patient's muscles located in vicinity of the skin region at which the PFA electrode patch is attached during the unipolar PFA treatment.

Example 26. The PFA electrode patch according to example 25, wherein the PFA electrode patch includes the motion sensor integrally coupled therewith.

Example 26. The PFA electrode patch according to example 25, wherein the PFA electrode patch is configured as a disposable patch, and wherein at least one of the following:

the PFA electrode patch includes the motion sensor as integral part thereof;

the PFA electrode patch serves as a disposable part of a PFA electrode patch assembly, which includes a reusable part attachable to the disposable part via the coupling member and includes the motion sensor thereon.

It should also be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof, which would occur to persons of ordinary skills in the art upon reading the description of the present invention and which are not disclosed in the prior art.

The invention claimed is:

1. A method for unipolar Pulse-Field Ablation (PFA), comprising:

providing a PFA system with a catheter having an electrode at its tip as a first pole, and at least two electrode patches on the patient's skin as return electrodes serving as second poles;

placing at least one motion sensor near the patient's body configured to identify spasm related motion patterns;

performing frequency analysis on output from the at least one motion sensor, wherein the analysis includes comparing amplitudes of frequency components of said output within a defined frequency range to a threshold;

based on the comparing, selecting at least one of the return electrodes for further pulse delivery.

2. The method of claim 1, wherein said at least one motion sensor comprises a position sensor and wherein said output is indicative of position changes of tissue near said at least one motion sensor respectively.

3. The method of claim 1, wherein at least one motion sensor comprises inertial measurement unit (IMU) and wherein said output is indicative of changes in velocity or acceleration of tissue near said at least one motion sensor respectively based on inertial measurements performed by said IMU.

4. The method of claim 3, wherein said inertial measurement unit (IMU) comprises at least one accelerometer.

5. The method of claim 1, wherein said at least one motion sensor is a wireless motion sensor comprising a wireless communication utility capable of wirelessly communicating said signals output to the PFA system.

6. The method of claim 1, wherein said spasm related motion patterns is associated with changes in at least one of a position, velocity and acceleration of the tissue near said at least one motion sensor.

7. The method of claim 6 wherein said processing comprises at least one of spectral analysis and filtering to identify said frequency components being within said frequency range.

8. The method of claim 1 wherein selecting the at least one return electrode based on the comparing, comprises carrying out the following upon identification of said spasm related motion pattern:

issuing an indication about the identified spasm related motion pattern; and responsive to said indication, obtaining user instructions for selection of the at least one return electrode;

thereby delivering said one or more PFA pulses or pacing signals via the at least one of the return electrodes in accordance with said user instructions.

9. The method of claim 1, wherein said selecting the at least one of the return electrodes is performed automatically based on performing the frequency analysis.

10. The method of claim 1, further comprising positioning the at least one motion sensor in at least one of the following:

at, or near, at least one respective electrode patch of said plurality of electrode patches;

at, or near, at least one region of interest of the subject's body at which spasm related motion pattern may occur due to nerve stimulation affected by said delivery of the PFA pulses or pacing signals.

11. The method of claim 1, wherein said selecting of the at least one of the return electrodes may include selection of more than one electrode patch to serve as said second pole.

12. The method of claim 11 wherein in case said more than one electrode patch are selected, said delivering of the PFA pulses or pacing signals comprises adjusting the relative portions of the said PFA pulses or pacing signals delivered through each of the selected electrode patches based on said monitoring, to thereby avoid or reduce spasm or other adverse effects of nerve stimulation.

13. The method of claim 1, wherein at least one of said electrode patches comprises a coupling member suitable for attachment of one of said at least one motion sensor thereto.

14. A system for unipolar pulse-field ablation (PFA), comprising:

a catheter with a tip electrode as a first pole;

at least two electrode patches configured to attach to a patient's skin and serve as return electrodes (second poles);

at least one motion sensor for placement near the patient's body and configured to identify spasm related motion patterns;

a pulse generator configured to deliver PFA pulses or pacing signals between the catheter electrode and one of the at least two electrode patches;

a processor configured to:

perform frequency analysis on output from the at least one motion sensor, wherein the analysis includes comparing amplitudes of frequency components of said output within a defined frequency range to a threshold;

based on the comparing, select at least one of the return electrodes for further pulse delivery.

15. The system of claim 14, wherein said at least one motion sensor comprises at least one of a position sensor and an inertial measurement unit.

16. The system of claim 14, wherein said at least one motion sensor is a wireless motion sensor, and the system comprising a wireless communication utility capable of wirelessly communicating with said at least one motion sensor to obtain therefrom the output indicative of motion sensed thereby.

17. The system of claim 14, wherein said spasm related motion patterns are associated with changes in at least one of a position, velocity and acceleration of the tissue near said at least one motion sensor.

18. The system of claim 14 comprising a user interface, and wherein said selecting the at least one return electrode based on the comparing comprises carrying out the following upon identification of said spasm related motion pattern:

operating said user interface to issue an indication about the identified spasm related motion pattern; and responsive to said indication, obtaining via said user interface, instructions for selection of the return electrodes;

thereby delivering said one or more PFA pulses or pacing signals via the at least one of the return electrodes in accordance with said instructions.

19. The system of claim 14 adapted for carrying out said automatically based on said monitoring of the spasm related motion patterns sensed by said at least one motion sensor.

20. The system of claim 14 adapted for connection with at least one motion sensor comprising at least one of the following:

at least one motion sensor arranged at, or near, at least one respective electrode patch of said plurality of electrode patches;

at least one motion sensor arranged at, or near, at least one region of interest of the subject's body at which spasm related motion pattern may occur due to nerve stimulation affected by said delivery of the PFA pulses or pacing signals.

21. The system of claim 14 wherein said selecting of the at least one of the return electrodes may include selection of more than one electrode patch to serve as said second pole.

22. The system of claim 21 wherein said signal switch is configured and operable to adjust relative portions of the said PFA pulses or pacing signals being delivered through each of the selected electrode patches; and in case said more than one electrode patch are selected, said processor adjusts said relative portions based on said monitoring, in order to avoid or reduce spasm near the selected electrode patches.

23. The system of claim 14 adapted to connect to at least one additional sensor capable of sensing additional effects of nerve stimulation due to said delivery of PFA pulses or pacing signals; and wherein said at least one processor is adapted to further monitor the signals obtained from said additional sensor and further select said certain one or more electrode patches based on the further monitoring of the signal from the additional sensor.

* * * * *